US00PP30758P3

(12) United States Plant Patent
Brown et al.

(10) Patent No.: US PP30,758 P3
(45) Date of Patent: Jul. 30, 2019

(54) APPLE TREE NAMED 'NY56'

(50) Latin Name: *Malus domestica*
Varietal Denomination: NY56

(71) Applicant: Cornell University, Ithaca, NY (US)

(72) Inventors: Susan Brown, Geneva, NY (US); Kevin Maloney, Phelps, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/732,410

(22) Filed: Nov. 7, 2017

(65) Prior Publication Data

US 2019/0141870 P1 May 9, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

U.S. PATENT DOCUMENTS

PP7,197 P 3/1990 Luby et al.

OTHER PUBLICATIONS

Clark et al. (2014). "Characterization of the defence response to *Venturia inaequalis* in 'Honeycrisp' apple, its ancestors, and progeny," European Journal of Plant Pathology, 140(1):69-81.
Hemmat et al. (2002). "Tagging and mapping scab resistance genes from R12740-7A apple," Journal of the American Society for Horticultural Science, 127(3):365-370.

*Primary Examiner* — Keith O. Robinson
(74) *Attorney, Agent, or Firm* — Morrison & Foerster LLP

(57) ABSTRACT

A new and distinctive variety of a *Malus domestica* apple tree named 'NY56', particularly characterized by its overall horticultural performance and consistency including resistance to apple scab and excellent fruit quality at harvest by having crisp, juicy and flavorful fruit, is disclosed.

8 Drawing Sheets

Latin name:
Botanical classification: *Malus domestica.*
Varietal denomination: The varietal denomination of the claimed apple tree variety is 'NY56'.

BACKGROUND OF THE INVENTION

Apples are an economically important crop. Accordingly, there exists a need to develop new varieties of apple tree with improved characteristics, such as fruit quality and disease resistance.

BRIEF SUMMARY OF THE INVENTION

In order to meet these needs, the present invention is directed to an improved variety of apple tree. In particular, the invention relates to a new and distinct variety of apple tree (*Malus domestica*), which has been denominated as 'NY56'. The new variety 'NY56' is resistant to the fungal pathogen *Venturia inaequalis* (apple scab), and produces fruit that is large in size, and crisp and mild in flavor, with a good balance of sweetness and acidity.

'NY56' was selected for its overall horticultural performance and consistency, including resistance to apple scab and excellent fruit quality (e.g., crisp, juicy and flavorful fruit at harvest), as compared to commercially available scab-resistant apple varieties, large fruit size, and good balance of sugar and acidity of the fruit.

Cultivation Summary

Apple tree 'NY56' is a hybrid that originated from a planned cross in 1994 in Geneva, N.Y. The seed parent (female parent) *Malus domestica* 'Honeycrisp' apple tree (U.S. Plant Pat. No. 7,197) is a popular commercial apple. The pollen parent (male parent) *Malus domestica* 'NY65707-19' apple tree (unpatented) is a proprietary advanced breeding selection that is resistant to the fungal disease apple scab.

The original cross designated '410' was made by applying pollen from a *Malus domestica* 'NY65707-19' apple tree onto emasculated flowers of a *Malus domestica* 'Honeycrisp' apple tree in Geneva, N.Y. in 1994. Seedlings of this progeny were inoculated with *Venturia inaequalis* at the first true-leaf stage, using the procedure described in Hemmat et al. (*Journal of the American Society for Horticultural Science,* 127(3), pp.365-370, 2002), except that a mixture of five races of *V. inaequalis* were used in inoculations. Seedlings that showed resistance to apple scab were planted on their own roots in an orchard in Geneva, N.Y. in 1995. One seedling, designated NY94410-56, was selected from field population of 165 seedlings on the basis of apple scab resistance, precocity, excellent fruit quality and attractive fruits. Additional trees of seedling NY94410-56 were produced by clonal propagation starting from 1999 and in subsequent years in Geneva, N.Y. These additional trees were evaluated for fruit and tree characteristics, pest resistance and trueness to type. NY94410-56 was later denominated as 'NY56'.

Asexual Reproduction

The progeny of 'NY56' was first asexually propagated by chip budding onto apple tree rootstock 'M.9' (unpatented) in 1999 in a research nursery in Geneva, N.Y. Subsequent asexual reproduction of 'NY56' has been successful using traditional methods of propagation (grafting and budding), demonstrating that the unique combination of traits of asexually propagated trees is identical in all appearances to the original tree.

Stability

Asexual reproduction of this new variety by grafting and budding onto rootstocks shows that the foregoing and all other characteristics and distinctions come true-to-form and are established and transmitted through succeeding propagations.

Distinguishing Characteristics of 'NY56'

Seed Parent—'Honeycrisp'

The seed parent *Malus domestica* 'Honeycrisp' is an apple tree variety known for its outstanding fruit quality, particularly characterized by having fruit with solid to mottled red color over a yellow background and a crisp and juicy fruit texture. When compared to 'Honeycrisp', 'NY56' has similarly low scion vigor and should be budded or grafted to a higher vigor rootstock to produce finished trees. Further, 'Honeycrisp' has a chlorotic leaf disorder that is seldom observed in 'NY56'. 'NY56' contains the $V_f$ gene that confers resistance to apple scab, whereas 'Honeycrisp' does not contain the $V_f$ gene. However, 'Honeycrisp' does contain other genes that confer scab resistance (Clark, M. D., Bus, V. G., Luby, J. J. and Bradeen, J. M., 2014. Characterization of the defence response to *Venturia inaequalis* in 'Honeycrisp' apple, its ancestors, and progeny. *European journal of plant pathology,* 140(1), pp.69-81.). 'NY56' has similar fruit quality characteristics to 'Honeycrisp' in its juiciness, crisp texture and large fruit size, however 'Honeycrisp' produces fruit that is earlier maturing and has a more blotchy and striped red coloring pattern. In addition, fruit of 'Honeycrisp' has a deeper basin depth and a green stem cavity russet color, whereas fruit of 'NY56' has a less deep basin depth and a tan stem cavity russet color.

Pollen Parent—'NY65707-19'

The pollen parent *Malus domestica* 'NY65707-19' is a proprietary advanced selection that is resistant to the fungal disease apple scab and contains the $V_f$ apple scab resistance gene. When compared to 'NY56', the pollen parent 'NY65707-19' produces fruit that is slightly more conic in shape, having slight ribbing, and exhibit a more typy appearance.

BRIEF DESCRIPTION OF THE DRAWINGS

The 'NY56' apple tree variety is illustrated by the accompanying photographs. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are seven years old for FIG. 1, and from trees that are 14 years old for FIG. 2 to FIG. 8.

FIG. 4A depicts a top view of the leaf. FIG. 4B depicts a bottom view of the leaf.

FIG. 6A depicts 'Honeycrisp'. FIG. 6B depicts 'NY56'. FIG. 6C depicts 'NY65707-19'.

FIG. 7A depicts a cross section of 'NY56' fruit cut longitudinally from top to bottom. FIG. 7B depicts a side view of the sun-exposed side of 'NY56' fruit. FIG. 7C depicts a stem and stem cavity of 'NY56' fruit. FIG. 7D depicts a cross section of 'NY56' fruit cut horizontally through the seed cavity. FIG. 7E depicts a side view of the shaded side of 'NY56' fruit. FIG. 7F depicts a calyx and basin area of 'NY56' fruit.

FIG. 8A depicts 'NY56'. FIG. 8B depicts 'Honeycrisp'.

DETAILED BOTANICAL DESCRIPTION

Figure 1:
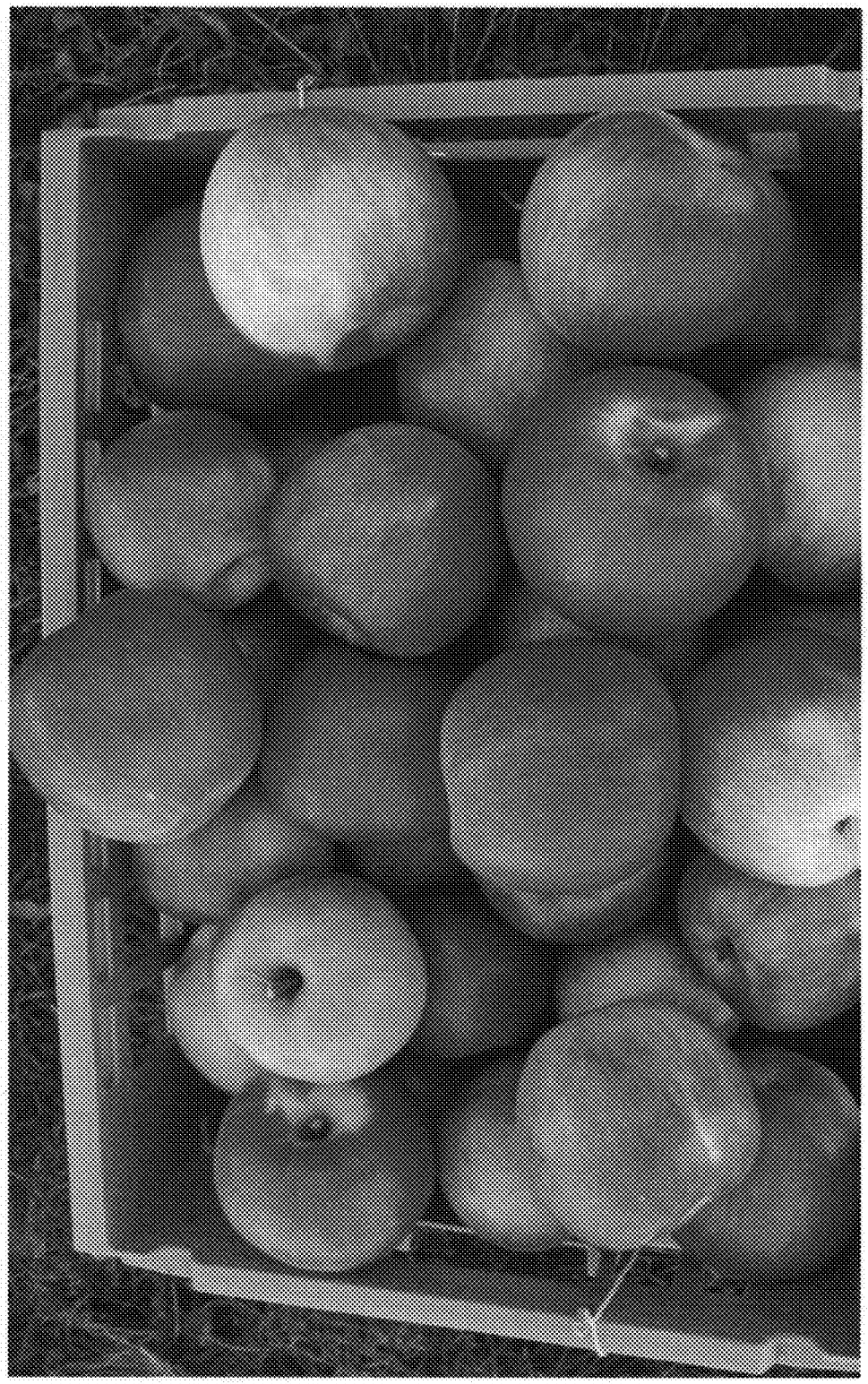
FIG. 1 depicts a bushel of fruit of apple tree variety 'NY56', depicting the range in fruit coloring and the typical fruit size and shape.
Figure 2:
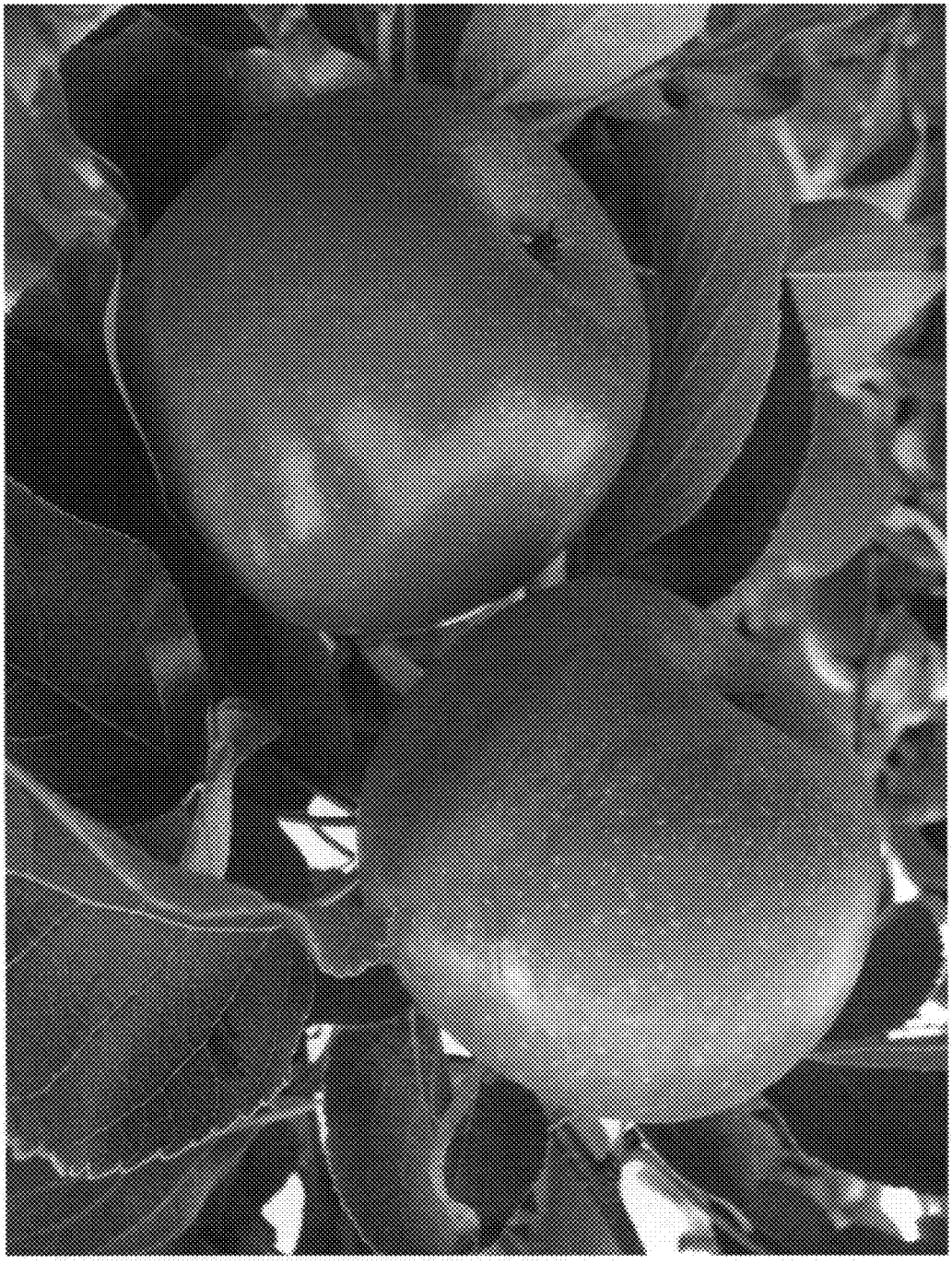
FIG. 2 depicts a close up of fruit of apple tree variety 'NY56' at harvest.
Figure 3:
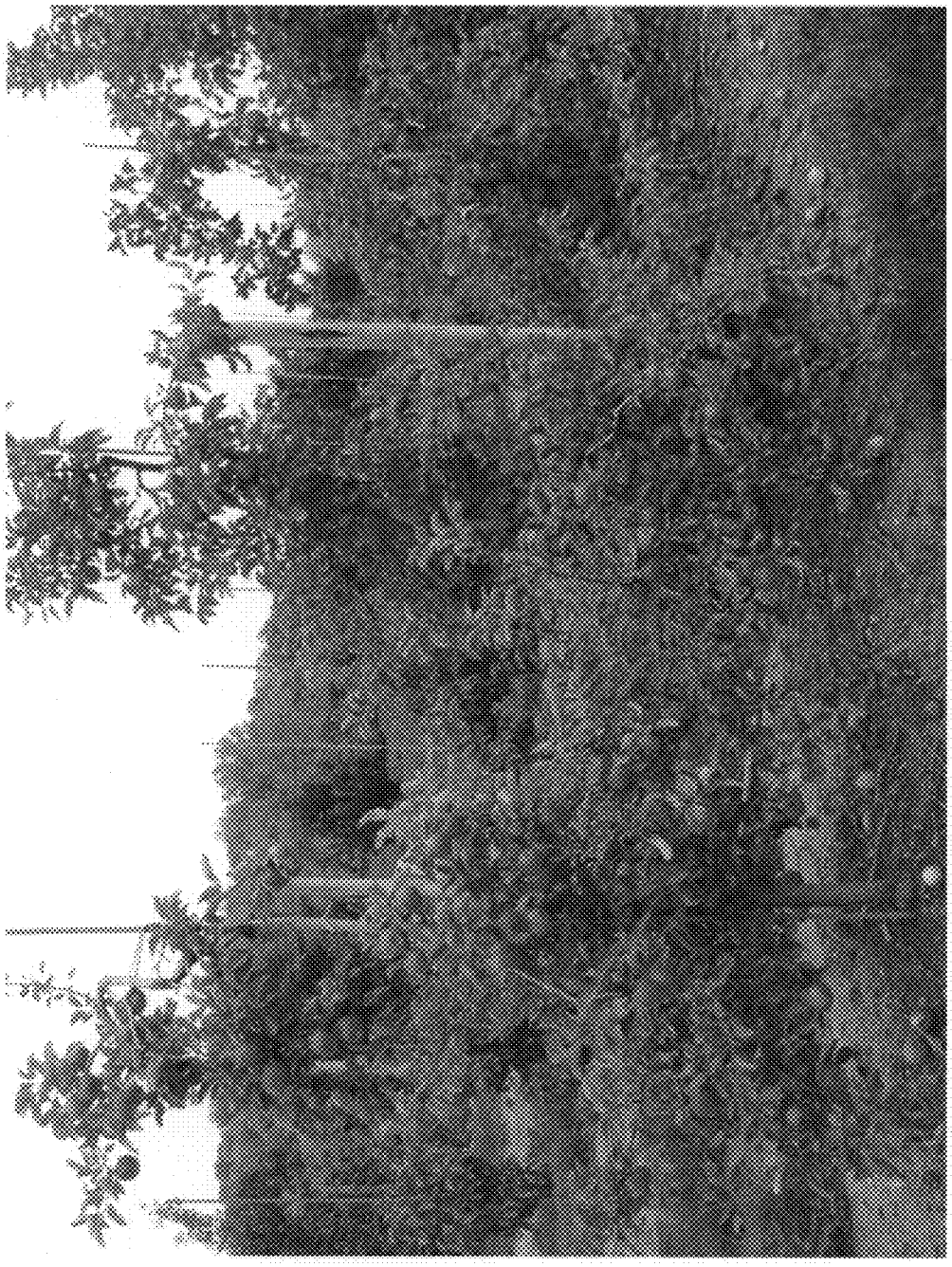
FIG. 3 depicts a row of trees of apple tree variety 'NY56' in orchard.
Figures 4A, 4B:
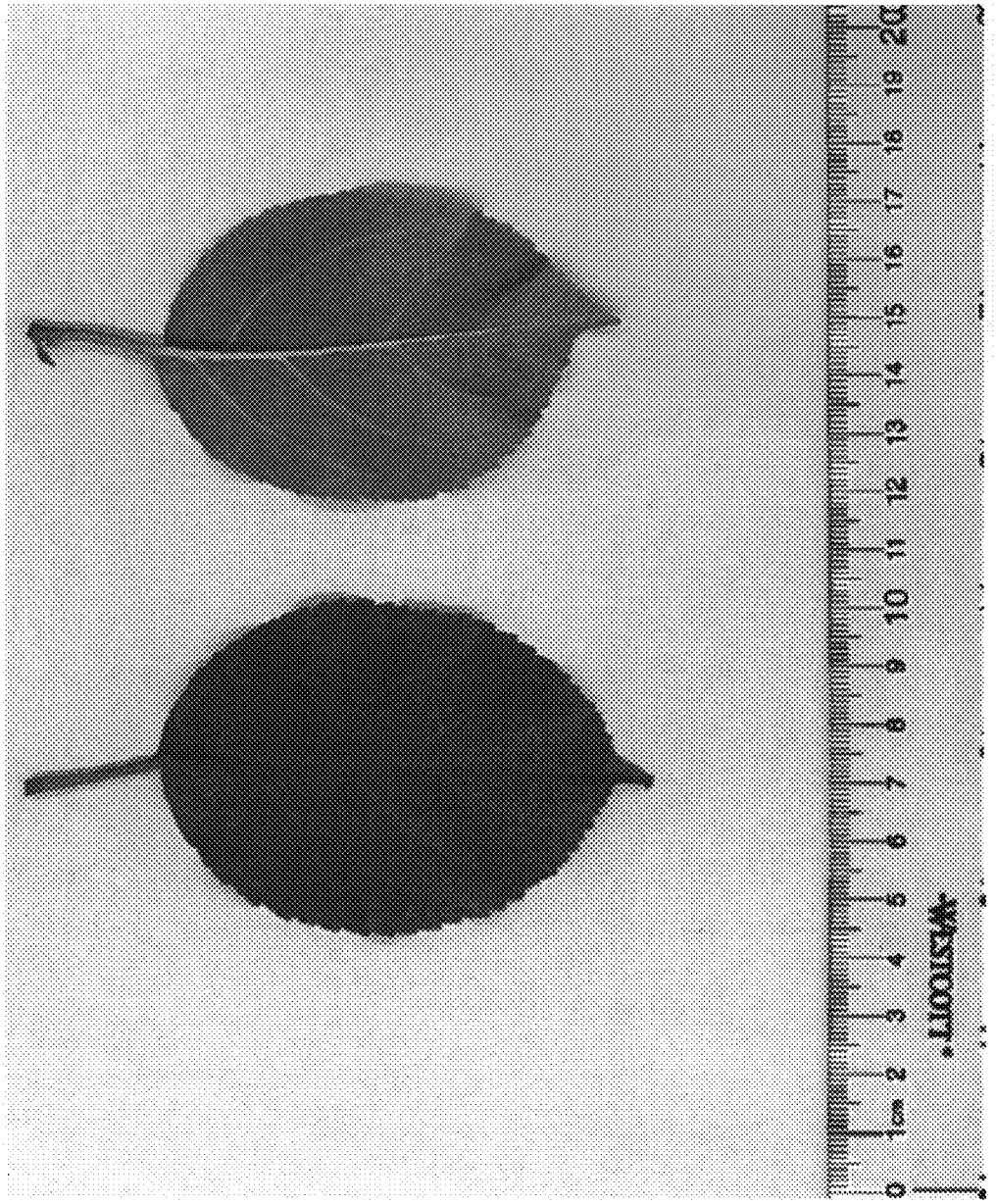
FIG. 4A and 4B depict a mature leaf of apple tree variety 'NY56'.
Figure 5:
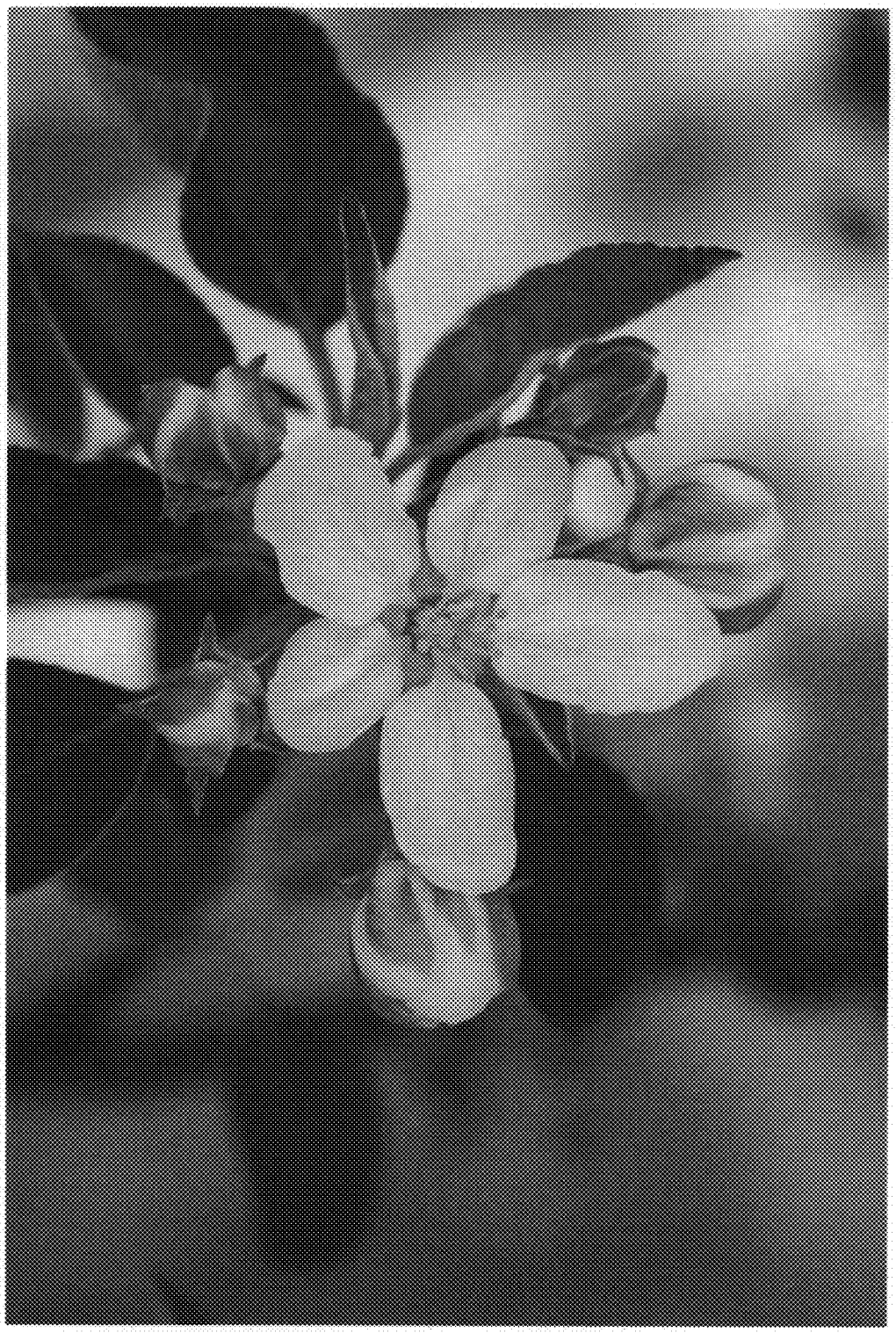
FIG. 5 depicts a flower cluster of apple tree variety 'NY56'.
Figures 6A, 6B, 6C:
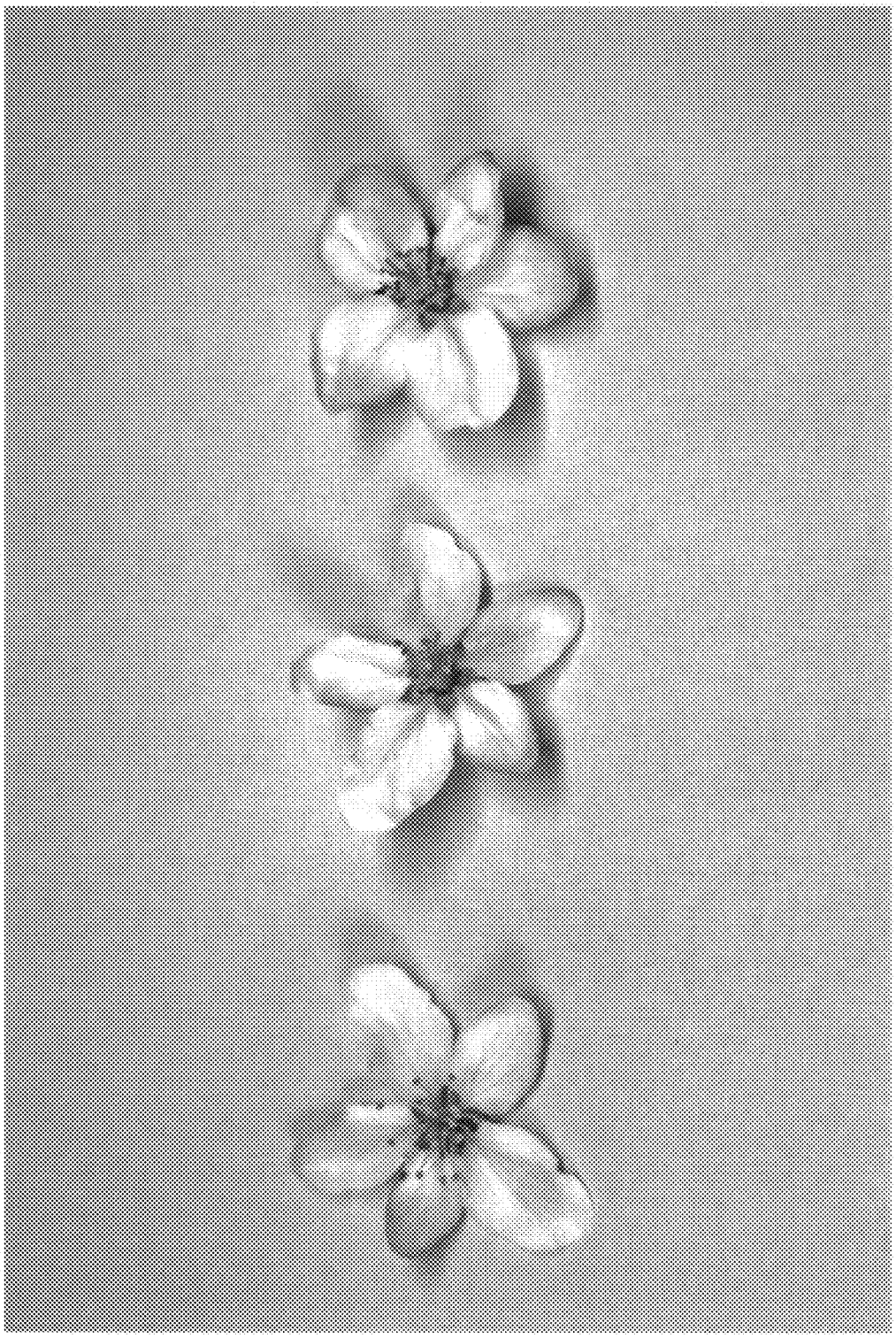
FIG. 6A to 6C depict a comparison of flowers between apple tree varieties 'Honeycrisp', 'NY56', and 'NY65707-19'.
Figures 7A, 7B, 7C, 7D, 7E, 7F:
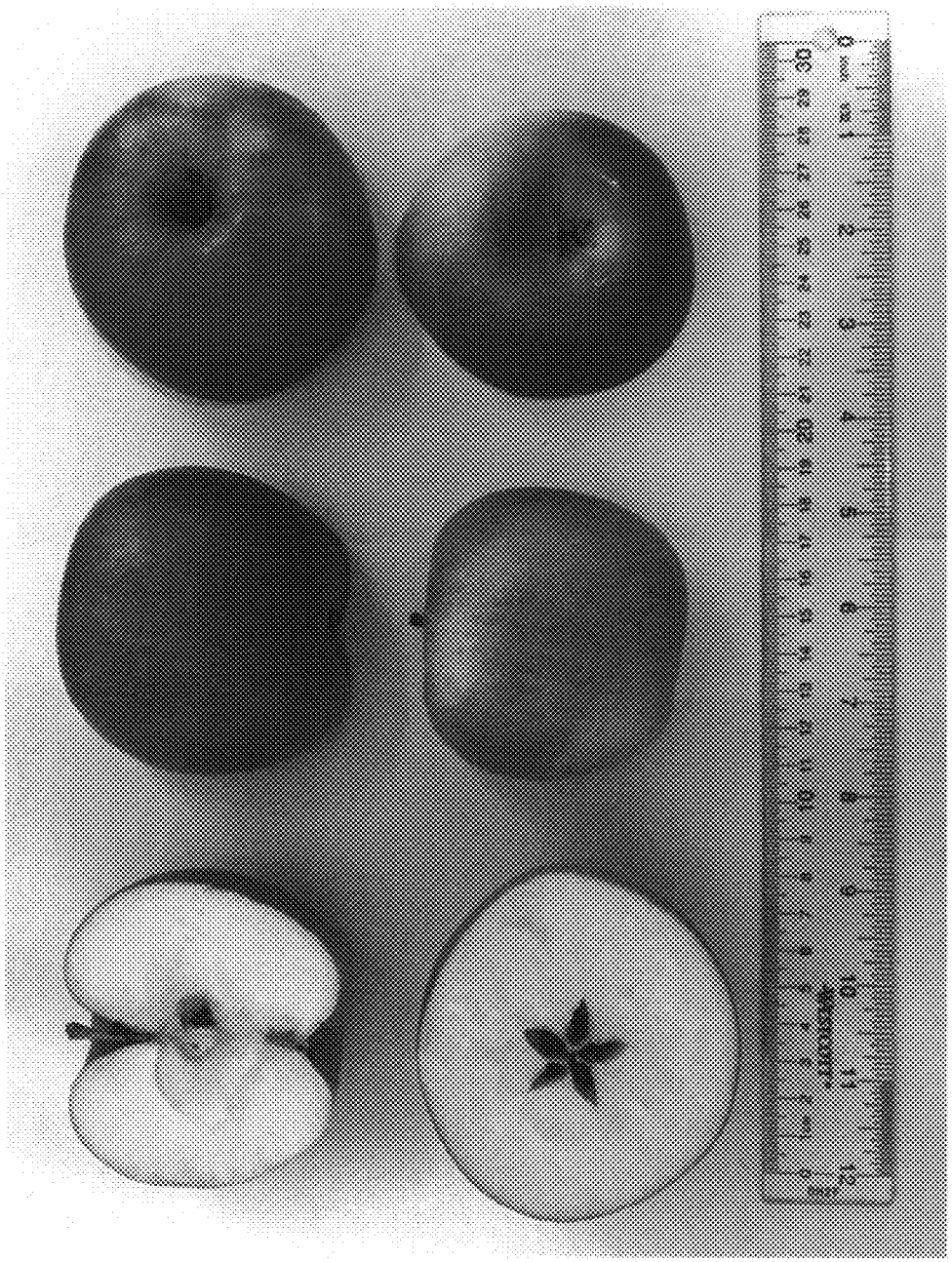
FIG. 7A to 7F depict six views of a typical fruit of apple tree variety 'NY56'.
Figures 8A, 8B:
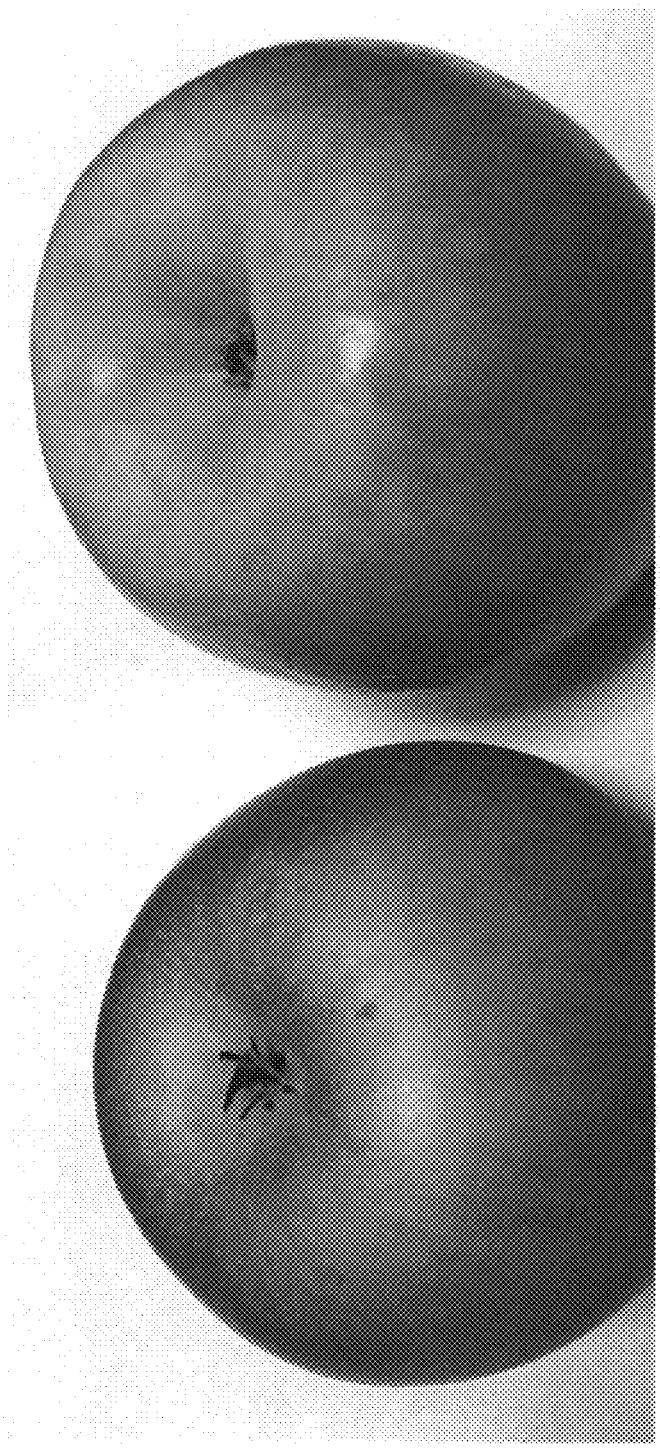
FIGS. 8A and 8B depict a comparison of fruit basin between apple tree varieties 'NY56' and 'Honeycrisp'.

The following description sets forth the distinctive characteristics of apple tree 'NY56'. The following description is based on the originally identified apple tree and asexually reproduced progeny grown in Geneva, N.Y., which is in USDA Plant Hardiness Zone 6A.

Referring more specifically to the details of the new and distinct apple tree variety 'NY56', unless otherwise stated, the following observations and characteristics have been taken since 1995 from a number of trees in different orchards in order to provide consistent descriptions.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart ($4^{th}$ Edition, published 2001).

Tree: Ramified tree type. Small to medium in size (mature trees on dwarf rootstocks have an average height of 3.2 m and spread of 2.1 m); standard upright habit; low vigor; early bearing on spurs. Trees are conducive to both free standing and trellis supported production systems.

Tree trunk: One-year-old dormant wood surface color is RHS 166A (Greyed-orange). Four-year-old dormant wood surface color is RHS 174A (Greyed-orange). Bark lenticels are small, round to oval in shape, average 6 per square centimeter, and range from 0.5 mm to 2.3 mm in diameter.

Branch: Branch diameter of four-year-old wood is 13.4 mm. Branch angle is flat, typically 5 degrees to 25 degrees above the horizontal. One-year-old shoots have an average internode length of 27 mm and 10 lenticels per square cm.

Leaf: Leaves are medium in size. Average leaf blade length is 87 mm and average blade width is 60 mm. Concavo-convex in cross section; upward in pose; medium glossiness of upward (adaxial) side; serrate margin indentation; average 3.1 serrations per centimeter. The color of the upper leaf blade surface is most similar to RHS 139A (Green) and the color of upper veins is RHS 145A (Yellow-green). The color of lower leaf blade surface is RHS 148B (Yellow-green) and the color of lower veins is RHS 145C (Yellow-green). Petioles are medium in length, with an average length of 25 mm. The color of petiole is RHS 191B (Greyed-green) and the color of the petiole base is RHS 183A (Greyed-purple). Stipules have an average length of 6.7 mm and an average width of 0.8 mm.

Flower: Flower color at the pink phenology stage is RHS 63A (Red-purple). Flower petals when open slightly overlap or have a space between them. Average flower width is 38 mm. There are five petals per flower. Petals are flat and wrinkled, cupped upward, wavy and slightly ribbed upward along midrib. Average petal length is 18 mm, and average width is 12 mm. Flower petals are white, some having a pink tinge. White coloring is RHS N155B (White) and RHS N155C (White) and pink coloring is RHS 51C (Red). Average flower pedicel length is 20 mm, and width 1.3 mm. Flower pedicel color is RHS 148B (Yellow-green). Anther color is RHS 162B (Greyed-yellow). There are 19 stamens per flower, each 6 to 11 mm long. Stamen color is RHS 145C (Yellow-green). Style is 11 mm long. Style number is five per flower. Style color is RHS 146D (Yellow green). Sepal length is 8 mm, and width is 4 mm. Sepal color is RHS 147C (Yellow-green) and tinged basally with a color of RHS 183B (Greyed-purple). Time of beginning of flowering: intermediate.

Fruit:

*Shape*.—Mostly conic, few are globose.

*Firmness*.—Average 15.8 pounds of pressure (range 13.1-20.0 pounds).

*Soluble solids*.—Average 13.3 Brix (range 11.2-15.7 Brix).

*Starch-iodine index ratings near maturity*.—Average 4.1 (range 2.0-7.3).

*Weight*.—Average 253 grams (range 203-303 grams).

*Diameter*.—Average 8.46 cm (range 7.9-8.8 cm).

*Height*.—Average 7.34 cm (range 6.7-8.0 cm).

*Juice pH*.—Average 3.5 (range 3.3-3.6).

*Color*.—Darkest fruit skin color is RHS 180A (Greyed-red); lighter fruit skin color is RHS 179B (Greyed-red). Fruit background color is RHS 151D (Yellow-green). Fruit lenticels are round, mostly dull and inconspicuous, with a color of RHS 161C (Greyed-yellow). There are on average 3.9 fruit skin lenticels per square centimeter. Fruit flesh color is RHS 155A (White).

*Bloom*.—Bloom of the fruit skin is weak.

*Flesh firmness*.—Fruit flesh is firm.

*Stem cavity* (*stalk*).—Acute, with a depth of 23.6 mm and a width of 33.8 mm.

*Stem*.—Average length is 19.1 mm and average thickness is 2.8 mm. Fruit stem color is RHS 152B (Yellow-green). Stem cavity russet color is RHS 199D (Grey-brown).

*Basin* (*eye*).—Abrupt, with medium to deep, broad breadth. Average basin depth is 19.5 mm and average basin width is 32.3 mm.

*Calyx*.—Persistent, closed, with erect lobes united at base.

*Calyx tube*.—Conical.

*Stamen remnants*.—Marginal.

*Carpels*.—Roundish, axile and emarginate.

*Core*.—Median and open.

*Core lines*.—Meeting.

*Locules*.—The aperture of the locules are moderately open.

*Seeds*.—Acute. Average 4.8 seeds per fruit; five locules per fruit; seed length 7.0 mm; width 5.0 mm; depth 3.0 mm; acuminate. Fresh seed color is RHS 166A (Greyed-orange), and dried seed color is RHS N199B (Grey-brown).

*Harvest time* (*eating maturity*).—Maturity is between October 2 and October 9 in a typical year in Geneva, N.Y.

*Keeping quality*.—Stores until the end of December.

*Fruit use*.—Multiple, e.g., fresh, slicing, and cider, etc.

Resistance to diseases and disorders: 'NY56' is resistant to *Venturia inaequalis* (apple scab). 'NY56' also appears to have good field resistance to cedar apple rust (CAR) caused by the fungal pathogen *Gymnosporangium juniper-virginianae* Sch. Bitter pit, storage rots, water core, brown core, scald and chilling temperature-related breakdown disorders have been observed at low amounts in certain years. Keeping quality in regular cold storage is up to 80 days.

Management: Trees require standard management for optimum tree growth and fruit quality. Trees require dormant pruning, fertilization, fruit thinning and pest control.

We claim:

1. A new and distinct variety of apple tree named 'NY56' as herein described and illustrated.

* * * * *